United States Patent
Janak

(10) Patent No.: US 9,750,258 B2
(45) Date of Patent: Sep. 5, 2017

(54) STABLE COMPOSITION FOR CONTROLLING BIOLOGICAL GROWTH AND METHOD FOR USING SAME IN OIL FIELD APPLICATIONS

(71) Applicant: Lonza Inc., Allendale, NJ (US)

(72) Inventor: Kevin E. Janak, Ossining, NY (US)

(73) Assignee: Lonza Inc., Allendale, NJ (US)

( * ) Notice: Subject to any disclaimer, the term of this patent is extended or adjusted under 35 U.S.C. 154(b) by 279 days.

(21) Appl. No.: 14/505,865

(22) Filed: Oct. 3, 2014

(65) Prior Publication Data

US 2015/0105353 A1 Apr. 16, 2015

Related U.S. Application Data

(60) Provisional application No. 61/890,659, filed on Oct. 14, 2013.

(51) Int. Cl.

| | | |
|---|---|---|
| *C23F 11/14* | (2006.01) | |
| *C09K 15/16* | (2006.01) | |
| *A01N 57/20* | (2006.01) | |
| *A01N 33/12* | (2006.01) | |
| *A01N 25/22* | (2006.01) | |
| *C02F 1/50* | (2006.01) | |
| *C09K 8/54* | (2006.01) | |
| *A01N 57/04* | (2006.01) | |

(52) U.S. Cl.
CPC ............ *A01N 57/20* (2013.01); *A01N 25/22* (2013.01); *A01N 33/12* (2013.01); *A01N 57/04* (2013.01); *C02F 1/50* (2013.01); *C09K 8/54* (2013.01); *C23F 11/141* (2013.01); *C09K 2208/32* (2013.01)

(58) Field of Classification Search
CPC ........ A01N 57/04; A01N 57/20; A01N 33/12; A01N 25/22; C02F 1/50; C09K 8/54; C09K 2208/32; C23F 11/141
USPC .................. 514/126; 252/390, 401
See application file for complete search history.

(56) References Cited

U.S. PATENT DOCUMENTS

| | | | |
|---|---|---|---|
| 4,673,509 A | | 6/1987 | Davis et al. |
| 5,741,757 A | * | 4/1998 | Cooper .................. A01N 57/20 504/153 |
| 6,419,879 B1 | | 7/2002 | Cooper et al. |
| 6,840,251 B2 | | 1/2005 | Gill et al. |
| 2004/0053793 A1 | | 3/2004 | Li et al. |
| 2006/0211584 A1 | | 9/2006 | Court et al. |
| 2007/0256987 A1 | | 11/2007 | Singleton et al. |
| 2012/0103919 A1 | | 5/2012 | Haggstrom et al. |
| 2014/0216748 A1 | | 8/2014 | Pou |

FOREIGN PATENT DOCUMENTS

| | | |
|---|---|---|
| FR | 2979632 | 3/2013 |
| GB | 2324467 | 10/1998 |
| WO | WO 2007/075681 | 7/2007 |
| WO | WO 2013/07811 | 1/2013 |

OTHER PUBLICATIONS

Search Report and Opinion for PCT/US2014/058938, dated Jan. 23, 2015.

Kramer, Jeffrey et al., "A New Performance Quaternary Phosphonium Biocide for Microbiological Control in Oilfield Water Systems," NACE International, Mar. 16, 2008.

* cited by examiner

*Primary Examiner* — David Karst
(74) *Attorney, Agent, or Firm* — Dority & Manning, P.A.

(57) ABSTRACT

A stabilized composition is disclosed which contains at least two biocides, particularly at least two non-oxidizing biocides. In one embodiment, the composition contains a phosphonium sulfate compound combined with a dialkyl dimethyl quaternary amine compound. In order to stabilize the composition, an alkyl trimethyl ammonium compound is added to the composition. In one embodiment, the stabilizing agent produces a single phase composition. With the aid of the stabilizing agent, the single phase concentrated compositions can be produced that can later be diluted for use. In one embodiment, the composition may be used to treat aqueous systems in industrial applications.

20 Claims, No Drawings

STABLE COMPOSITION FOR CONTROLLING BIOLOGICAL GROWTH AND METHOD FOR USING SAME IN OIL FIELD APPLICATIONS

CROSS-REFERENCE TO RELATED APPLICATIONS

The present application claims priority to U.S. Provisional Application Ser. No. 61/890,659 having a filing date of Oct. 14, 2013, which is incorporated herein by reference in its entirety.

BACKGROUND

Microbiologically Influenced Corrosion (MIC) is a significant problem within the oil and gas industry. It is estimated that as many as 20 to 30% of pipeline corrosion failures may be attributed to MIC. MIC is usually defined as a specific type of corrosion influenced by the presence or activity of microorganisms including bacteria and fungi. The primary pathway by which MIC occurs is via development of a community of microorganisms on a surface such as a pipe within an organic matrix commonly referred to as a biofilm.

Biofilm consists of cells immobilized in a substratum, frequently embedded in an organic polymer matrix of microbial origin, which can restrict the diffusion of substances and bind antimicrobials. It is estimated that more than 99% of all the planet's bacteria live in biofilm communities. In flowing aquatic environments, a biofilm consists of a sticky and absorptive polysaccharide matrix encompassing microorganisms. Biofilm bacteria are morphologically and metabolically distinct from free-floating bacteria. Their structural organization is a characteristic feature and distinguishes biofilm cultures from conventional planktonic organisms.

One of the most important strategies in mitigating MIC is the removal of biofilm or prevention of biofilm formation. However, control of biofilms and sessile bacteria is much more difficult to achieve than control of planktonic cells, primarily due to the presence of the exogenous polymeric matrix. This is due, in part, to the dynamic nature of biofilms, whereby biofilms continuously change in thickness, surface distribution, microbial populations and chemical composition, and respond to changes in environmental factors such as water temperature, water chemistry and surface conditions. Thus, the complexity of biofilms reduces the effectiveness of typical chemical treatment and removal strategies.

This reduced efficacy is evidenced by the typically much higher concentrations of chemical biocides required for biofilm removal and control relative to control of planktonic organisms. This can increase both the cost of treatment and may also add an additional concern of corrosion due to extraordinarily high concentrations of corrosive chemical biocides.

In this regard, several biocides are used for MIC control in oil field gathering lines. Commonly used biocides are non-oxidizing chemicals such as glutaraldehyde or bis[tetrakis(hydroxymethyl)phosphonium] sulfate (THPS). Some concern has arisen that these biocides may be inherently corrosive at high end use concentrations and could cause general corrosion in the assets they are protecting from MIC.

Another group of biocides used in industry are quaternary amines. However, quaternary amines used alone at reasonable and affordable treatment concentrations are generally not as effective as other biocides in controlling microorganisms attached to metal surfaces and bulk fluids.

In view of the above, a need exists for an improved composition for preventing and inhibiting biofilm growth in industrial systems, particularly in oil field applications.

SUMMARY

In general, the present disclosure is directed to a method for preventing and eradicating biofilm growth in industrial systems, such as in oil field applications. The present disclosure is also directed to a composition for preventing or inhibiting biofilm growth. The composition can be used in aqueous systems to control pitting, corrosion, and the like in various tubes, pipes and tiles, especially those made from metals.

In one embodiment, the composition comprises a first non-oxidizing biocide combined with a second non-oxidizing biocide. The first biocide may comprise a phosphonium sulphate salt such as bis[tetrakis(hydroxymethyl)phosphonium] sulphate. The second biocide, on the other hand, may comprise a quaternary amine salt, such as one having the following formula:

$$(R^1R^2R^3R^4N^+)_n X^{n-} \qquad (I)$$

wherein $R^1$ through $R^4$ are independently selected from the group consisting of $C_{1\text{-}20}$ aliphatic hydrocarbyl groups and $C_{7\text{-}11}$ aromatic hydrocarbyl groups, and $X^{n-}$ is a counter-anion selected from the group consisting of carbonate, bicarbonate, halides, phosphates, ethosulfates, citrates, borates, nitrate, $C_{1\text{-}20}$ carboxylates, and mixtures thereof, wherein n designates the number of negative charges of the counter-anion.

In accordance with the present disclosure, the composition further comprises a stabilizing agent. The first biocide and the second biocide, for instance, may be incompatible or immiscible at higher concentrations. The presence of the stabilizing agent, however, can produce a single phase solution.

In one embodiment, the stabilizing agent comprises an alkyl trimethyl ammonium compound which refers to an alkyl trimethyl ammonium or a salt thereof. The stabilizing agent is different than the second biocide and is added in an amount sufficient for the first biocide and the second biocide to be miscible in a single solution.

In one embodiment, the composition may be relatively concentrated containing a total active concentration of greater than about 15% by weight, such as greater than about 18% by weight, such as greater than about 20% by weight, such as even greater than about 25% by weight. The total active concentration is generally less than 60% by weight, such as less than 50% by weight, such as less than 40% by weight. As used herein, the total active concentration is the total amount of non-oxidizing biocides contained in the composition. When formulated in a concentrated state, the composition can be diluted later when used in an aqueous system.

The present disclosure is also directed to a process for preventing biofilm growth. The process includes adding to an aqueous medium contained in an industrial system the composition as described above. In one embodiment, the composition described above can be diluted prior to being added to the aqueous medium. In addition, the composition or diluted composition may be combined with various other components prior to being added to the aqueous medium. For instance, the composition may be combined with a corrosion inhibitor, a scale inhibitor, at least one surfactant, a neutralizing agent, a coupling agent, a dispersing agent, a foam inhibitor, a viscosity modifier, a chelating agent, a dye, or mixtures thereof.

Other features and aspects of the present disclosure are discussed in greater detail below.

DETAILED DESCRIPTION

It is to be understood by one of the ordinary skill in the art that the present discussion is a description of exemplary embodiments only, and is not intended as limiting the broader aspects of the present disclosure.

The extent and nature of MIC vary with the context of the problem. The diverse nature of physico-chemical conditions in oil field applications, as well as diverse microbiology and environments in which biofilms grow call for a variety of tactics and strategies for MIC control that might include corrosion inhibitors, microbiological control, biofilm control and prevention, pipe cleaning, pigging, and mixtures thereof.

The present disclosure is directed to an improved composition and process for preventing the growth of biofilms in aqueous systems, such as those related to oil field applications. In accordance with the present disclosure, a first biocide is combined with a second biocide. The combination of biocides can provide various advantages and benefits. For instance, using a combination of biocides can provide greater efficacy over a larger range of microorganisms. In addition, biocides can be selected that are complementary to each other. For instance, in one embodiment, a non-oxidizing biocide, such as a phosphonium sulphate salt, may be combined with a second biocide comprising a quaternary ammonium compound.

Unfortunately, however, many biocides are incompatible when mixed together. For instance, a phosphonium sulphate salt is generally incompatible in a solution with a quaternary ammonium compound, and particularly a dialkyl dimethyl quaternary amine compound, especially at higher concentrations. Consequently, the two biocides have a tendency to separate from each other making application of the biocides to an aqueous system problematic.

In accordance with the present disclosure, however, a stabilizing agent is added to the blend of biocides. The stabilizing agent, in one embodiment, produces a single phase solution, even when the biocides are present at a relatively high concentration.

In one embodiment, the stabilizing agent may comprise a hydrotrope that stabilizes the blends of biocides providing a product that can be more readily shipped and diluted. A single phase solution can be produced without having to add additional co-solvents or without having to use expensive polymers.

In one embodiment, the stabilizing agent may comprise an alkyl trimethyl ammonium compound, such as an alkyl trimethyl ammonium salt. When added to an aqueous composition containing a phosphonium sulphate salt and a dialkyl dimethyl quaternary amine compound, the stabilizing agent can produce a clear concentrate, even at total active concentrations of greater than about 15% by weight, such as greater than about 20% by weight, such as even greater than about 25% by weight.

As described above, the composition in the present disclosure contains a first non-oxidizing biocide, at least a second non-oxidizing biocide, and a stabilizing agent. The first non-oxidizing biocide may include, for instance, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, Poly(oxyethylene(dimethyliminio)ethylene(dimethyliminio)ethylene dichloride, methylene bisthiocyanate, 2-decylthioethanamine, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin) oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one. In one embodiment, the first biocide may comprise a phosphorous compound, such as a phosphonium compound.

The phosphorus compound may contain one phosphorus atom and may be of the formula $[HORPR'_{-n}O_m]_y X_x$ wherein n is 2 or 3; m is 0 or 1 such that (n+m)=2 or 3; x is 0 or 1 such that (n+x)=2 or 4; y is equal to the valency of X; R is an alkylene group of 1 to 4, preferably 1, carbon atoms with the hydroxy group attached to the 1, 2, 3 or 4 numbered carbon atom; each R' may be the same or different and represents an alkyl or alkenyl group, preferably of 1-4 carbon atoms, or more usually a group of formula HOR—, wherein R is as defined above; and X is anion such that the phosphorus compound is water soluble. Thus the (—ROH) group may be a 1-, or 2-hydroxyalkyl group e.g. a hydroxy methyl, 1 or 2 hydroxy ethyl 1 or 2 hydroxypropyl or 1 or 2 hydroxy-butyl group; preferably at least one R' is ROH, but may be for example a methyl, ethyl, propyl, iso propyl, or n-sec-, iso- or tert-butyl group. X may be a monovalent anion such as a chloride or bromide, or an organic carboxylate, e.g. an alkane carboxylate, preferably of 2-5 carbon atoms such as acetate, bisulphite or bisulphate or an organic sulphonate such as methosulphate or a benzene, toluene or xylene sulphonate or a dihydrogen phosphate, or a divalent anion such as sulphate or sulphite or monohydrogen phosphate or a trivalent group such as phosphate or organic carboxylates with 2 or more carboxyl groups such as citrate. The phosphorus compound may also be a phosphine oxide.

The phosphorus compound may alternatively contain 2 or more phosphorus atoms, so long as the phosphorus compound is water soluble to a concentration of at least 0.5 g/l at 25° C. Such phosphorus compounds contain at least 1 hydroxy alkyl group, usually per phosphorus atom, and preferably at least 2 hydroxyalkyl groups per phosphorus atom. Such hydroxyalkyl groups are preferably of formula ROH, where R is as defined above. The group or groups joining the phosphorus atoms together may of formula —R—, —R—O—, —R—O—R— or —R—NH—R or —R—R"—R— where R is as defined above and R" is the residue formed by removal of two hydrogen atoms, bonded to nitrogen, from a di or polyamide or di or poly amine, such as urea, dicyandiamidae, thiourea or guanidine. Such compounds with 2 or more, e.g. 3, hydroxyalkyl groups per phosphorus atom may be made by self condensation of compounds with 3 or 4 hydroxyalkyl groups attached to one phosphorus atom, e.g. of formula $[HOR\ P\ R'_{-n}O_m]_y X_x$ or with a compound of formula $R"H_2$ such as urea.

Preferably the phosphorus compound contains only one phosphorus atom and 3 or 4 hydroxyalkyl groups especially hydroxymethyl groups. Such compounds are made by reacting phosphine with an aldehyde usually formaldehyde or a ketone in the presence of mineral acid usually hydrochloric, sulphuric or phosphoric acid. Depending on the proportions the product may be a tris hydroxyalkyl phosphine or tetrakis (hydroxyalkyl) phosphonium salt; however, the latter tends to be converted to the former under aqueous alkaline conditions with small amounts of the dimeric compound with 2 phosphorus atoms and an ROR bridge and/or the phosphine oxide with n=2, m=1, x=0. The phosphorus compound usually has a pH of 1-6, when in 75% by weight aqueous solution. The phosphorus compounds in which one or more of $R_1$ are alkyl groups are made from the corresponding alkyl substituted phosphines by reaction with the aldehyde or ketone. To avoid foaming, any alkyl or alkenyl groups present can have less than 5 carbon atoms. However compounds in which 1 or 2 alkyl or alkenyl groups per molecule have up to 24 carbon atoms are effective biocides and may be used in applications where foaming does not present a problem.

Thus specific examples of biocides include tetrakis (hydroxymethyl) phosphonium sulphate, tetrakis (hydroxymethyl) phosphonium chloride, tetrakis (hydroxymethyl) phosphonium phosphate and tris (hydroxymethyl) phosphine oxide as preferred examples and dodecyl tris (hydroxymethyl) phosphonium chloride or oleyl tris (hydroxymethyl) phosphonium sulphate as other examples. In one particular embodiment, the first biocide comprises bis [tetrakis(hydroxymethyl)phosphonium] sulphate.

The second biocide present in the composition, on the other hand, may comprise at least one quaternary ammonium compound. The at least one quaternary ammonium compound can have the following formula:

$$(R^1R^2R^3R^4N^+)_nX^{n-} \qquad (I)$$

where R1 through R4 are independently selected from the group consisting of $C_{1-20}$ aliphatic hydrocarbyl groups and $C_{7-11}$ aromatic hydrocarbyl groups, and $X^{n-}$ is a counter-anion selected from the group consisting of carbonate, bicarbonate, halides, phosphates, ethosulfates, citrates, borates, nitrate, and $C_{1-20}$ carboxylates. Especially preferred counter-anions $X^{n-}$ are carbonate, bicarbonate, and mixtures thereof.

Quaternary ammonium compounds as identified above have a natural affinity to metal. It is believed that the quaternary ammonium compounds reside at the surface of metals and block oxygen and/or air from causing further oxidation of the metal surface. The above action of the compound can also prevent or inhibit biofilm growth. Quaternary ammonium compounds, for instance, can prevent the growth of surface-bound sulfate reducing bacteria and acid producing bacteria.

In one embodiment, the second biocide may comprise a quaternary amine salt, such as a dialkyl dimethyl quaternary amine compound, such as a dialkyl dimethyl quaternary amine salt.

In one embodiment, the salt comprises a halide, such as a chloride. Each alkyl group in the dialkyl dimethyl quaternary amine compound can have a carbon chain length of from about about 4 carbon atoms to about 48 carbon atoms, such as from about 6 carbon atoms to about 28 carbon atoms. In one particular embodiment, the carbon chain length is from about 8 carbon atoms to about 20 carbon atoms. In one particular embodiment, for instance, a didecyl dimethyl ammonium salt is used.

In addition to a first biocide and a second biocide, the composition may include further biocides. For instance, a mixture of quaternary amine compounds, such as a mixture of dialkyl dimethyl quaternary amine compounds, may be present in the composition in conjunction with the first biocide, which may comprise a phosphonium sulfate salt.

The relative amounts of each biocide present in the composition can vary depending upon numerous factors and the end use application. In one particular embodiment, when combining a phosphonium sulfate salt with a dialkyl dimethyl quaternary amine compound, the first biocide and the second biocide may be present in the composition at a weight ratio of generally less than about 10:1. For instance, the weight ratio may be from about 10:1 to about 1:1.

The concentration of the first biocide, such as a phosphonium salt, can be in the range of 50-2000 ppm, preferably in the range of 75-1000 ppm, and most preferably in the range of 125-500 ppm and the concentration of the second biocide, such as a quaternary ammonium salt, is in the range of 25-1000 ppm, preferably in the range of 37-500 ppm, and most preferably in the range of 63-250 ppm.

In accordance with the present disclosure, the composition further contains a stabilizing agent that increases the compatibility of the first biocide and the second biocide. In one embodiment, a stabilizing agent is present in an amount sufficient such that the resulting composition comprises a single phase solution. In one embodiment, the stabilizing agent may comprise a quaternary amine compound that is different from the second biocide present in the composition. In one particular embodiment, for instance, the stabilizing agent may comprise an alkyl trimethyl ammonium compound, such as an alkyl trimethyl ammonium salt. When present as a salt, for instance, the alkyl trimethyl ammonium compound may comprise a halide, such as a chloride salt. The alkyl group contained in the alkyl trimethyl ammonium compound may have a carbon chain length of from about 4 carbon atoms to about 48 carbon atoms, such as from about 6 carbon atoms to about 28 carbon atoms, such as from about 8 carbon atoms to about 20 carbon atoms.

The stabilizing agent is present in the composition in an amount sufficient, in one embodiment, to produce a single phase solution, even when the total active concentration of the different biocides contained within the composition is greater than about 10% by weight, such as greater than 15% by weight, such as greater than 20% by weight, such as even greater than about 25% by weight. The total active concentration in the composition is generally less than about 60% by weight, such is less than about 50% by weight, such as less than about 40% by weight.

Through the use of a stabilizing agent in accordance with the present disclosure, a concentrated composition can be produced and shipped to a location where the composition is used. Once present at the location, the composition can then be diluted and fed to an aqueous system, such as fed to an aqueous medium that is part of an industrial system. In one embodiment, for instance, the aqueous system may be part of an oil field application.

When fed to an aqueous system, the composition may be combined with various other components. For instance, when used in oil field applications, a corrosion inhibitor, an anti-foaming agent, a chelating agent, an anti-static agent, one or more surfactants, a dispersing agent, an anti-scaling agent, and mixtures thereof may be combined with the composition.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A composition for preventing biofilm growth comprising:
a first non-oxidizing biocide blended with a second non-oxidizing biocide, the second biocide comprising a quaternary ammonium compound, the first biocide and the second biocide being blended with a stabilizing agent, the stabilizing agent comprising an alkyltrimethylammonium compound that is different than the second biocide,
wherein the first biocide and the second biocide are present in the composition at concentrations such that the biocides are immiscible,
wherein the composition has a total active concentration of greater than 15% by weight, and
wherein the stabilizing agent is present in an amount sufficient to produce a single phase solution.

2. A composition as defined in claim 1, wherein the first biocide comprises a phosphonium sulfate salt.

3. A composition as defined in claim 2, wherein the first biocide comprises bis[tetrakis(hydroxymethyl)phosphonium] sulfate.

4. A composition as defined in claim 1, wherein the second biocide comprises a dialkyldimethylammonium compound.

5. A composition as defined in claim 1, wherein the first biocide and the second biocide are present in the composition at a ratio of from about 10:1 to about 1:1.

6. A composition as defined in claim 1, wherein the composition is polymer-free.

7. A composition as defined in claim 1, wherein the second biocide comprises a monomeric dialkyldimethylammonium compound.

8. A composition as defined in claim 1, wherein the second biocide comprises a quaternary ammonium compound of the formula

$$(R^1R^2R^3R^4N^+)_n X^{n-} \qquad (I)$$

wherein $R^1$ through $R^4$ are independently selected from the group consisting of $C_{1-20}$ aliphatic hydrocarbyl groups and $C_{7-11}$ aromatic hydrocarbyl groups, and $X^{n-}$ is a counter-anion selected from the group consisting of carbonate, bicarbonate, halides, phosphates, ethosulfates, citrates, borates, nitrate, $C_{1-20}$ carboxylates, and mixtures thereof, wherein n designates the number of negative charges of the counter-anion.

9. A composition as defined in claim 8, wherein $X^{n-}$ comprises a halide.

10. A composition as defined in claim 1, wherein the alkyl group in the alkyl trimethyl ammonium compound has a carbon chain length of from about 4 carbon atoms to about 48 carbon atoms.

11. A water treatment composition for oil field applications comprising the composition as defined in claim 1 blended with a corrosion inhibitor.

12. A water treatment composition as defined in claim 11, further comprising an anti-foaming agent, a chelating agent, an anti-static agent, a surfactant, a dispersing agent, a scale inhibitor or mixtures thereof.

13. A process for producing a water treatment composition for oil field applications comprising diluting the composition defined in claim 1 with a carrier comprising water and adding the diluted composition to a water source.

14. A process as defined in claim 13, further comprising the step of adding to the diluted composition a corrosion inhibitor, a scale inhibitor, an anti-foaming agent, a chelating agent, an anti-static agent, a surfactant, a dispersing agent, or mixtures thereof.

15. A composition as defined in claim 1, wherein the composition has a total active concentration of greater than 18% by weight.

16. A composition as defined in claim 15, wherein the first biocide and the second biocide are present in the composition at a ratio of from about 10:1 to about 1:1.

17. A method of controlling biofilm growth in an industrial system comprising adding to an aqueous medium in the industrial system a composition comprising a first non-oxidizing biocide blended with a second non-oxidizing biocide, the second biocide comprising a quaternary ammonium compound, the first biocide and the second biocide being blended with a stabilizing agent, the stabilizing agent comprising an alkyltrimethylammonium compound that is different than the second biocide,
wherein the first biocide and the second biocide are present in the composition at concentrations such that the biocides are immiscible,
wherein the composition has a total active concentration of greater than 15% by weight, and
wherein the stabilizing agent is present in an amount sufficient to produce a single phase solution.

18. A process as defined in claim 17, the process further comprising the step of diluting the composition prior to adding the composition to the aqueous medium.

19. A process as defined in claim 17, wherein the composition is combined with a corrosion inhibitor, a scale inhibitor, an anti-foaming agent, a chelating agent, an anti-static agent, a surfactant, a dispersing agent, or mixtures thereof.

20. A process as defined in claim 17, wherein the first biocide comprises a phosphonium sulphate salt and the second biocide comprises a dialkyl dimethyl quaternary ammonium compound and wherein the first biocide and the second biocide are contained in the composition at a weight ratio of from about 10:1 to about 1:1.

* * * * *